United States Patent [19]
Knapp et al.

[11] Patent Number: 5,491,492
[45] Date of Patent: * Feb. 13, 1996

[54] METHOD AND APPARATUS FOR EYE TRACKING FOR CONVERGENCE AND STRABISMUS MEASUREMENT

[75] Inventors: R. Benjamin Knapp; Lisa E. Hake, both of Sebastopol; Hugh S. Lusted, Sausalito, all of Calif.

[73] Assignee: Biocontrol Systems, Inc., Palo Alto, Calif.

[ * ] Notice: The portion of the term of this patent subsequent to Mar. 8, 2011, has been disclaimed.

[21] Appl. No.: 182,295

[22] Filed: Jan. 12, 1994

Related U.S. Application Data

[62] Division of Ser. No. 831,561, Feb. 5, 1992, Pat. No. 5,293,187.

[51] Int. Cl.⁶ .................................................. A61B 3/14
[52] U.S. Cl. .............................. 345/8; 351/210; 351/209
[58] Field of Search ............................. 345/8, 157, 156; 351/209, 210, 246

[56] References Cited

U.S. PATENT DOCUMENTS

| | | |
|---|---|---|
| 3,462,604 | 8/1967 | Mason . |
| 3,507,988 | 4/1970 | Holmes . |
| 3,724,932 | 4/1973 | Cornsweet et al. ......................... 351/7 |
| 3,986,030 | 10/1976 | Teltscher ................................. 250/349 |
| 4,081,623 | 3/1978 | Vogeley . |
| 4,109,145 | 8/1978 | Graf ....................................... 250/201 |
| 4,576,184 | 3/1986 | Westerman ............................... 128/733 |
| 4,582,403 | 4/1986 | Weinblatt ................................. 351/210 |
| 4,651,145 | 3/1987 | Sutter ..................................... 345/156 |
| 4,735,498 | 4/1988 | Uddén et al. ............................ 351/210 |
| 4,836,670 | 6/1989 | Hutchinson .............................. 351/210 |
| 4,838,681 | 6/1989 | Pavlidis .................................. 351/210 |
| 4,866,229 | 9/1989 | Scharfenberg ....................... 350/208 R |
| 5,367,315 | 11/1994 | Pan ........................................ 345/156 |

FOREIGN PATENT DOCUMENTS

| | | |
|---|---|---|
| 0055338 | 7/1982 | European Pat. Off. . |
| 0281717 | 9/1988 | European Pat. Off. . |
| 0463340 | 1/1992 | European Pat. Off. . |
| 9117705 | 11/1991 | WIPO . |

*Primary Examiner*—Ulysses Weldon
*Assistant Examiner*—Matthew Luu
*Attorney, Agent, or Firm*—John P. O'Banion

[57] ABSTRACT

A method and apparatus for determining the position of each eye of a human operator (12) with respect to a fixed reference point or with respect to each other by using electro-oculogram signals produced by eye movement. Human operator (12) wears sensor assembly (10) which includes a plurality of sensors (14) which are arranged to monitor right and left, as well as horizontal and vertical eye movement. The sensed electro-oculogram signals are processed by a microprocessor (60) into separate positional signals representing upward movement, downward movement, movement to the left, movement to the right, convergence, and divergence. These positional signals are used to control three dimensional imagery on a computer, video game, or other apparatus to be controlled, or for strabismus measurement and diagnosis.

6 Claims, 7 Drawing Sheets

METHOD AND APPARATUS FOR EYE TRACKING FOR CONVERGENCE AND STRABISMUS MEASUREMENT

CROSS REFERENCE TO RELATED APPLICATIONS

This is a divisional of application Ser. No. 07/831,561 filed on Feb. 5, 1992, now U.S. Pat. No. 5,293,187.

BACKGROUND OF THE INVENTION

1. Field of the Invention

This invention relates generally to techniques and devices for tracking eye movement, and more specifically to a method and apparatus for sensing electro-oculogram (EOG) signals produced by eye movement and processing those signals to determine the horizontal and vertical position of each eye as well to determine convergence or divergence of the eyes. The signals representing eye position are interfaced to an output device for strabismus measurement or for controlling a video game or other electronic device.

2. Description of the Background Art

Over the past several years interactive video games have gained widespread popularity. Stand-alone game units have been installed in arcades, restaurants, movie theaters, and other publicly accessible facilities. Additionally, video game units have entered the home entertainment market in the form of adapters for standard television sets. As technology has progressed, there has been interest in "virtual reality" where video games take on a three-dimensional character. These games, however, require the use of the hands in their operation thereby making hand/eye coordination essential to successful play. By using movement of the eyes alone to play the game, a higher degree of realism can be achieved.

Several types of systems have been developed over the years to permit computers or machinery to be controlled by eye movement. For example, U.S. Pat. No. 3,462,604 issued to Mason on Aug. 19, 1969, discloses an oculometer for determining eye orientation based on light reflected from the retina of the eye relative to light reflected from the front surface of the eye. Light is directed to the eyeball where it is reflected by both the front surface and the retina at the back of the eye. A detecting system views the reflected images and determines eye position from the relative positions of the reflected images.

U.S. Pat. No. 4,109,145 issued to Graf on Aug. 22, 1978, discloses an apparatus for "line of sight" detection of eye orientation. Using an oculometer or other line of sight determining device to monitor the orientation of the eye, the apparatus measures the length of time that the operator's eye remains in the line of sight position relative to a particular control function. If the line of sight position is maintained longer than a predetermined time, the apparatus produces a control output.

U.S. Pat. No. 3,986,030 issued to Teltscher on Oct. 12, 1976, discloses an eye-motion operable keyboard accessory for paraplegics or other incapacitated persons. The apparatus includes a light source for directing light toward the operator's eye and a plurality of light responsive sensors which are activated by light reflected from the operator's eye. The sensors are connected to a keyboard actuated instrument to be controlled by the eye movement.

U.S. Pat. No. 4,081,623 issued to Vogeley on Mar. 28, 1978, discloses the use of a light source, a radiation sensor, a command discriminator and a display unit to detect when the operator blinks his eyes in a particular coded sequence. The eye blinking is decoded and used to dial a telephone or control a piece of machinery.

U.S. Pat. No. 3,507,988 issued to Holmes on Apr. 21, 1970, discloses a narrow-band television system which has resolution characteristics similar to those of the human eye and which is capable of highly resolving a portion of the transmitted field, the location of which is variable in accordance with the line of sight of an observer. Eye position is determined through the use of reflected light.

U.S. Pat. No. 3,724,932 issued to Cornsweet et al. on Apr. 3, 1973, discloses an apparatus wherein the eye is flooded with light so that a plurality of Purkinje images are formed by the reflecting surfaces of the eye. Two of the Purkinje images are monitored by imaging them on a rotating disc which has a plurality of orthogonal slits through which the Purkinje images are further imaged on a photodetector. The orientation of the optic axis of the eye is determined by monitoring the separation of the Purkinje images.

U.S. Pat. No. 4,866,229 issued to Scharfenberg on Sep. 12, 1989, discloses an apparatus for projecting optical information to a headset so that the wearer can view images which are separate from or superimposed on the directly visible surrounding view.

U.S. Pat. No. 4,651,145 issued to Sutter on Mar. 17, 1987, discloses an oculo-encephalographic communication system in which visual stimuli with unique code signals is presented to the operator and the electro-encephalographic (EEG) signal of the operator is monitored. The code can be identified by the EEG signal of the operator and, therefore, a character on a display can be selected simply by looking at it.

U.S. Pat. No. 4,576,184 issued to Westerman on Mar. 18, 1986, discloses an apparatus for detecting drug ingestion based upon the corneo-retinal potential and/or brain waves using an electro-nystagmograph (ENG) machine.

The disadvantage of many of the systems disclosed in the foregoing patents is that they use light reflected from the eye and are susceptible to interference from other light sources. Other systems require particular visual stimuli to be presented to the operator and corresponding reaction codes to be monitored.

The deficiencies in the foregoing devices can be overcome by using electro-oculogram signals, which represent an electrical signature of eye movement. Co-pending application Ser. No. 07/077,733 filed on Jul. 24, 1987, now Ser. No. 07/784,147, discloses methods and apparatus for using electro-oculogram and other biopotential signals to generate music and to control video devices. Co-pending application Ser. No. 07/557,205 filed on Jul. 24, 1990, discloses methods and apparatus for using electro-oculogram and other biopotential signals to control the cursor on a video display or to operate a video game by merely looking at a particular position on the video display. In these methods and apparatus, however, electro-oculogram signals are generated by eye movement when the eyes are aligned and, in effect, present two-dimensional movement (left/right and up/down). They do not have three-dimensional movement capability or the capability to determine the exact position of each eye independently with relation to a fixed point of reference. See also, Hugh S. Lusted and R. Benjamin Knapp, "Music Produced by Human Bioelectric Signals," presented to the 155th Meeting of the American Association for the Advancement of Science, San Francisco, Calif. on Jan. 18, 1989.

Strabismus, which is a medical condition wherein the eyes do not maintain horizontal or vertical alignment when they are moved, is difficult to measure with accuracy. In order to diagnose the degree of strabismus, it is necessary to determine the position of each eye independently in relation to a fixed reference point. The present invention provides accurate measurement of the position of each eye.

The foregoing patents and publications reflect the state of the art of which the applicant is aware and are tendered with the view toward discharging applicants' acknowledged duty of candor in disclosing information which may be pertinent in the examination of this application. It is respectfully stipulated, however, that none of these patents or publications teach or render obvious, singly or when considered in combination, applicants' claimed invention.

SUMMARY OF THE INVENTION

The present invention relates generally to the operation of three-dimensional games and devices and strabismus measurement by determining the independent position of each eye.

Three-dimensional imagery is typically visually presented to a viewer with lenses or a split-screen viewer in order to provide a separate image to each eye. The "depth" dimension is created by presenting each eye with separate images, and the two images are offset to create an illusion of parallax. In fusing the images, the brain creates the third or "depth" dimension from the video screen. The present invention takes horizontal movement measurements for each eye independently and generates signals dependent upon the degree of eye convergence. The convergence signals are processed and sent to the image computer which, on command, will move the virtual object "forward" or "backward" in the visual field by changing the parallax offset of the left and right eye images. When used in conjunction with two-dimensional video games, the convergence signals can be used to change levels in the game, jump to hyperspace, or serve to control any other function.

Strabismus, on the other hand, is a physiological condition of non-alignment of the eyes. Clinically, this condition is difficult to measure. However, with the present invention, the horizontal and vertical positions of each eye with respect to a fixed reference point can be independently measured for diagnostic purposes.

The principle behind the invention disclosed herein is the sensing of electro-oculogram (EOG) signals produced by eye movement. An EOG signal represents an electrical "signature" of eye movement. The present invention uses sensors positioned on the head of the user to detect EOG signals representing horizontal and vertical eye movement, as well as convergence or divergence of the eyes. The EOG signals are amplified and processed to extract features useful for mapping to output commands, such as controlling the position of a cursor on a computer screen or determining the position of each eye in relation to a fixed reference point for purposes of strabismus measurement. A digital signal processor gives flexibility to the system by allowing various characteristics of the EOG signals to be mapped to various selectable output devices.

An object of the invention is to use electro-oculogram signals to detect eye movement.

Another object of the invention is to use electro-oculogram signals to determine whether a person's eyes are converged or diverged.

Another object of the invention is to use electrooculogram signals to determine the horizontal or vertical position of an eye in relation to a fixed reference point.

Another object of the invention is to determine the position of an eye independently from the position of the other eye.

Another object of the invention is to control the cursor position on a computer video display by moving the operator's eyes.

Another object of the invention is to control three-dimensional imagery on a computer video display by using convergence of the operator's eyes.

Another object of the invention is to use electro-oculogram signals for making strabismus measurements.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 2:
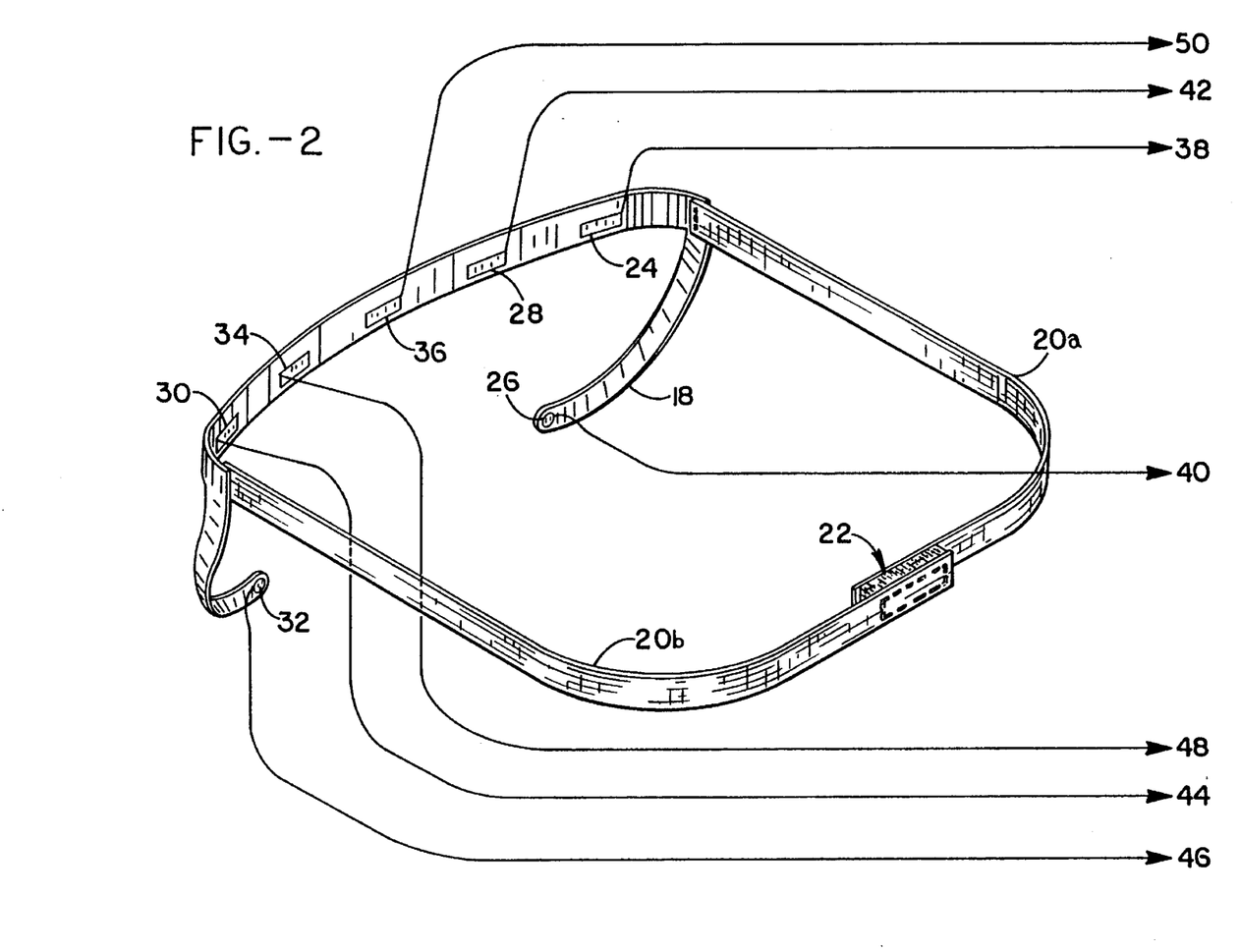
FIG. 2 is a perspective view of the sensor headband of the present invention diagrammatically depicting connection leads from individual sensors.
Figure 3A:
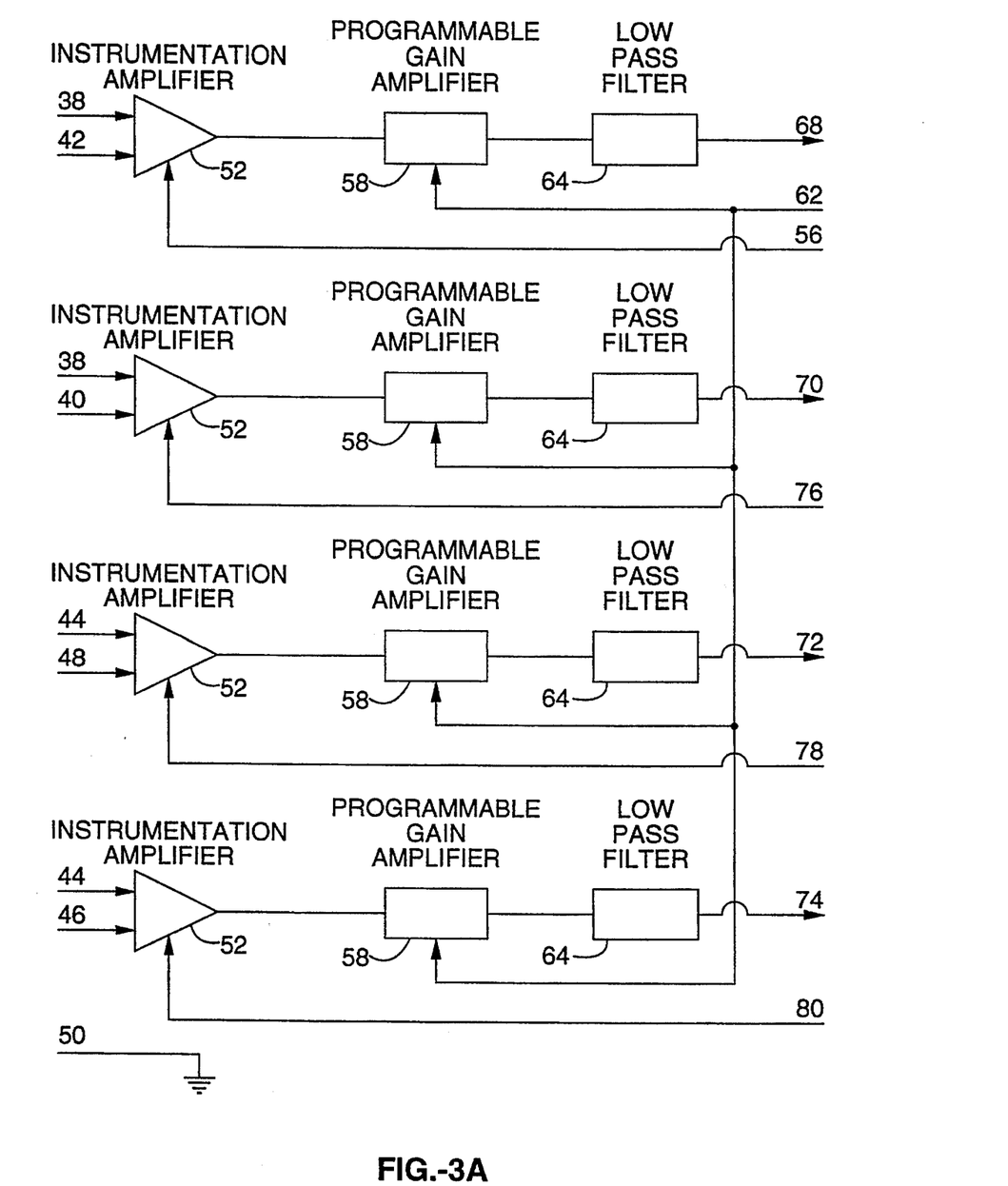
FIG. 3A and 3B are a functional block diagram of the electrical components of the present invention.
Figure 3B:
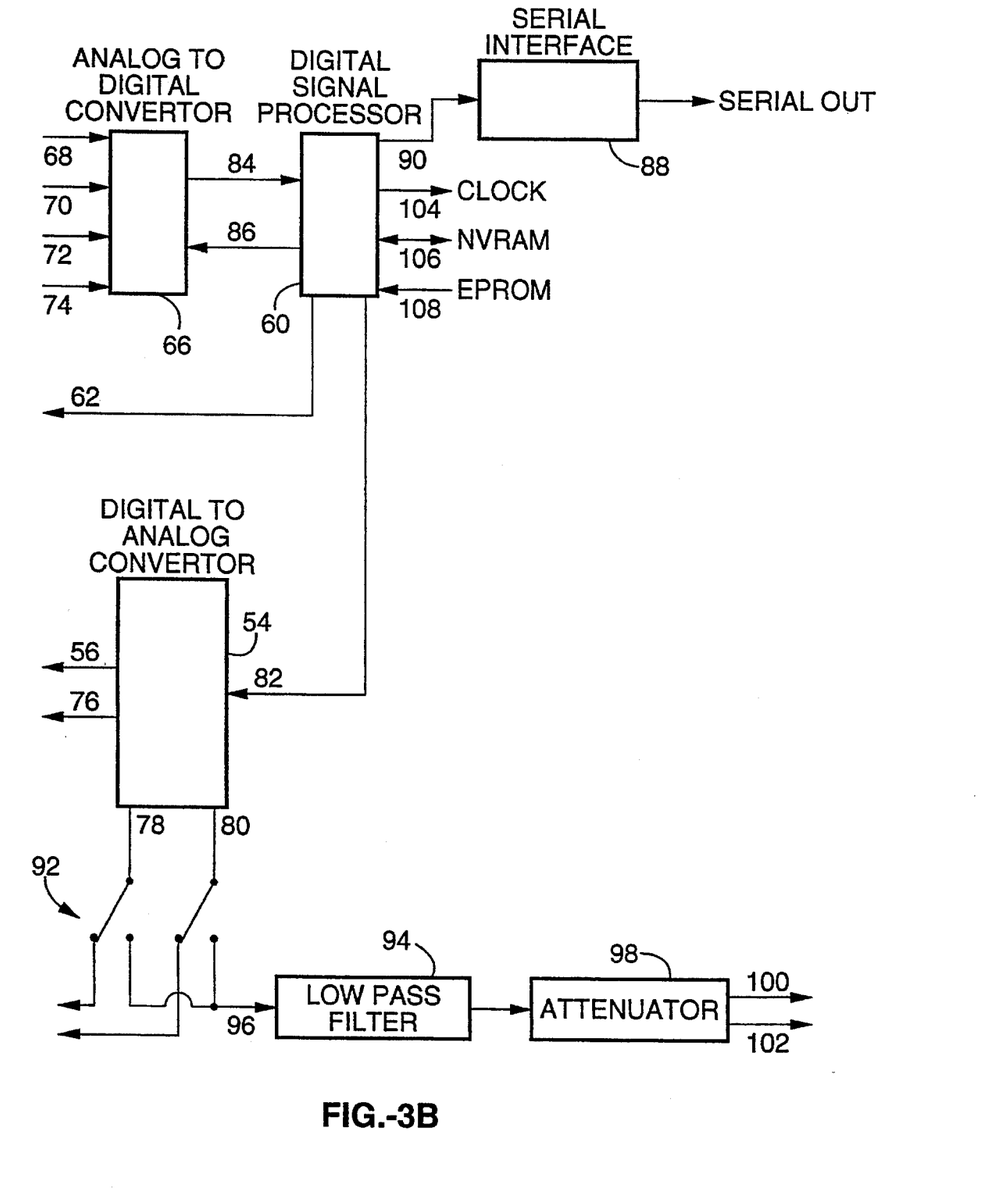
Figure 4:
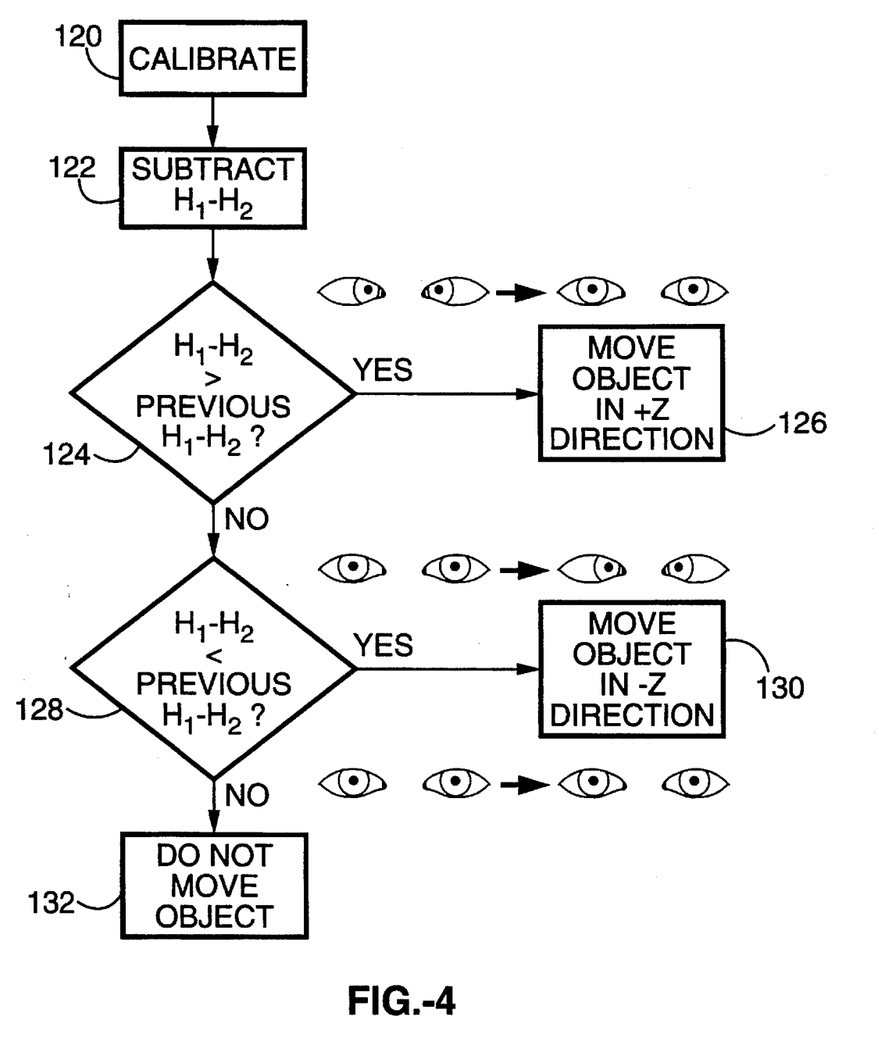
FIG. 4 is a flow chart showing the sequence of steps in the present invention to determine convergence of the eyes for controlling an output device.
Figure 5:
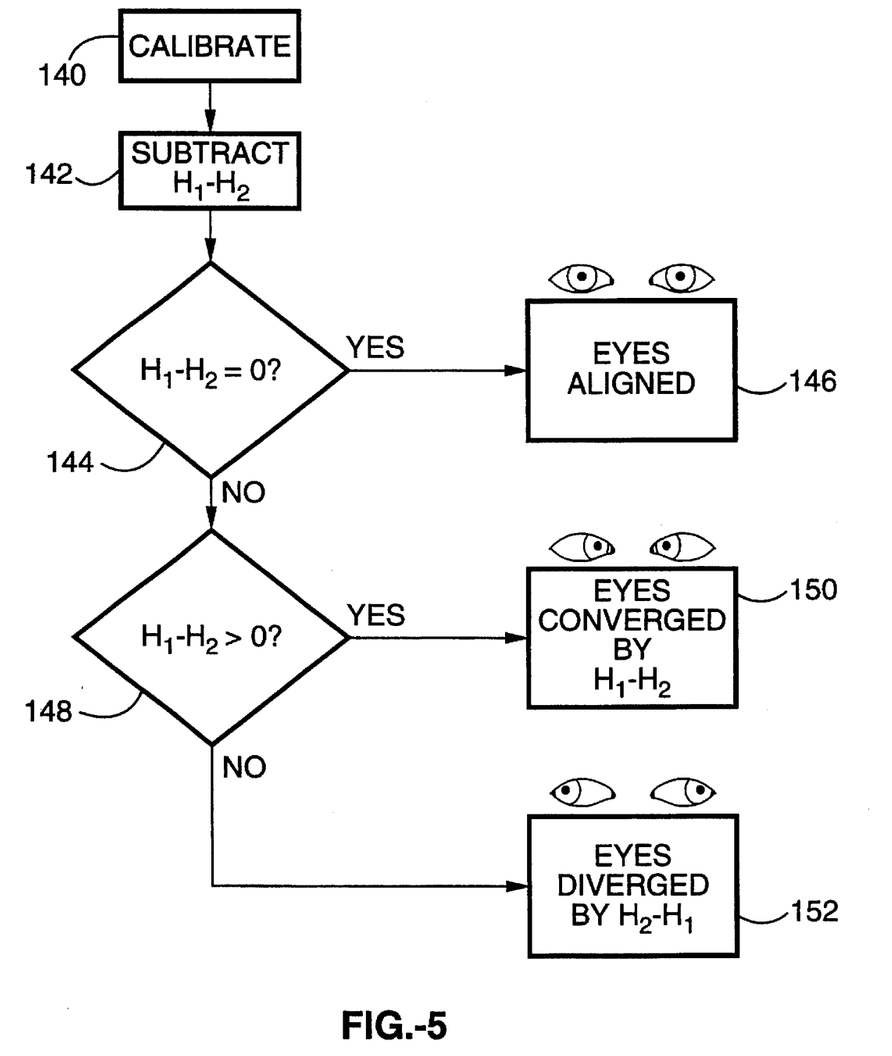
FIG. 5 is a flow chart showing the sequence of steps in the present invention to determine convergence or divergence of the eyes for strabismus measurements.
Figure 6:
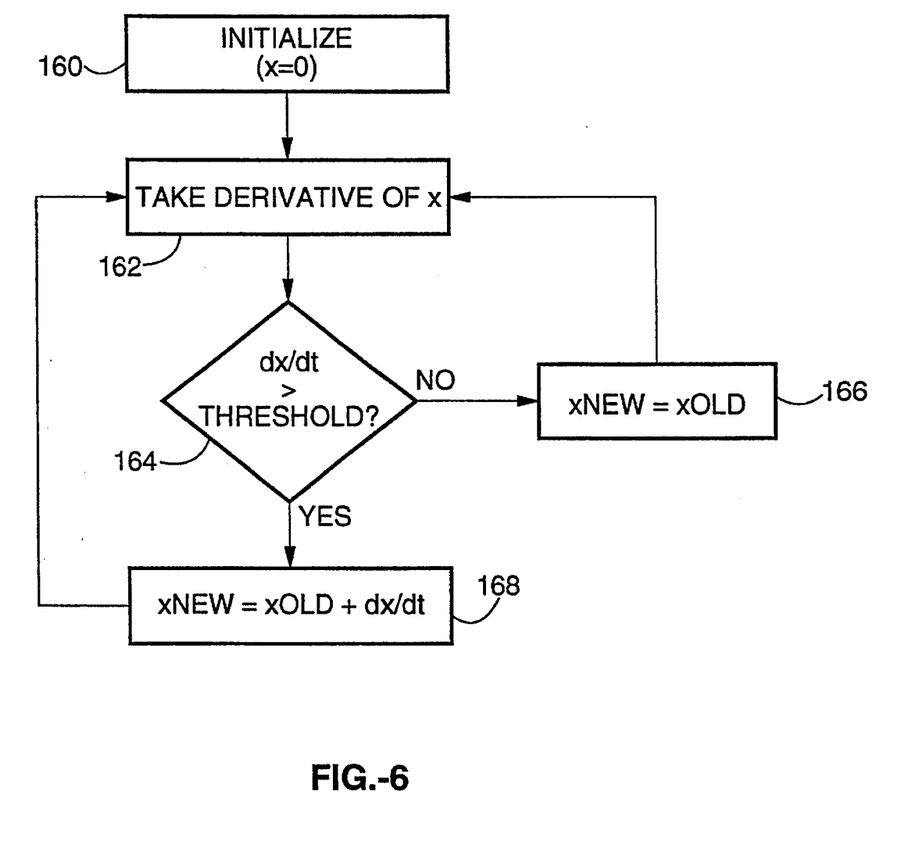
FIG. 6 is a flow chart showing the sequence of steps in the present invention for drift compensation.

Referring more specifically to the drawings, for illustrative purposes the present invention is embodied in the apparatus generally shown in FIG. 1 through FIG. 3B and the methods generally shown in FIG. 4 through FIG. 6. It will be appreciated that the apparatus may vary as to configuration and as to details of the parts without departing from the basic concepts as disclosed herein, and that the methods may vary as to individual steps without departing from the basic concepts as disclosed herein.

An electro-oculogram (EOG) is a record of an electrical trace created by the movement of a human eyeball in relation to the head. The EOG is recorded by placing electrodes around the eyes, detecting the signal produced from eye movement, and amplifying and filtering the electro-physiological signal. To detect vertical movement, electrodes are placed above and below the position of the eyes. To detect horizontal movement, electrodes are placed above the eyes at lateral positions.

An EOG signal is created as the eye moves within the electrical field detected by the electrodes. The eye itself acts as a dipole (or battery). The cornea relates to the positive pole while the retina relates to the negative pole.

For example, if electrodes are located symmetrically on either side of the eyes, when an eye is looking straight ahead the dipole is at right angles to the electric field detected by the electrodes and the resultant output is zero. When the eye moves, there exists a voltage shift with reference to the straight ahead position.

Eye movements cause a direct current voltage shift which can occur as rapidly as one fiftieth of a second (50 Hz) over full range, in effect producing a time varying shift relative to the steady state output (straight ahead position). The signals are very low in amplitude and must be amplified and filtered to render them useable. Additionally, the amplifiers used should have good low frequency response to prevent signal loss.

It is important to note that, to render an EOG signal usable, it is necessary to filter out other physiologically produced signals. For example, an EOG signal is distinguishable from an electro-encephalographic (EEG) signal in amplitude and frequency. An EEG signal is a brain wave signal which is much higher in frequency and arises from large populations of nerve cells in the brain firing synchronously. EEG signals are typically recorded from sensors placed on the scalp and are much lower in amplitude than EOG signals (100 microvolts for EEG contrasted to 1 millivolt for EOG). Thus EOG and EEG signals can be separated by frequency and amplitude.

Figure 1:
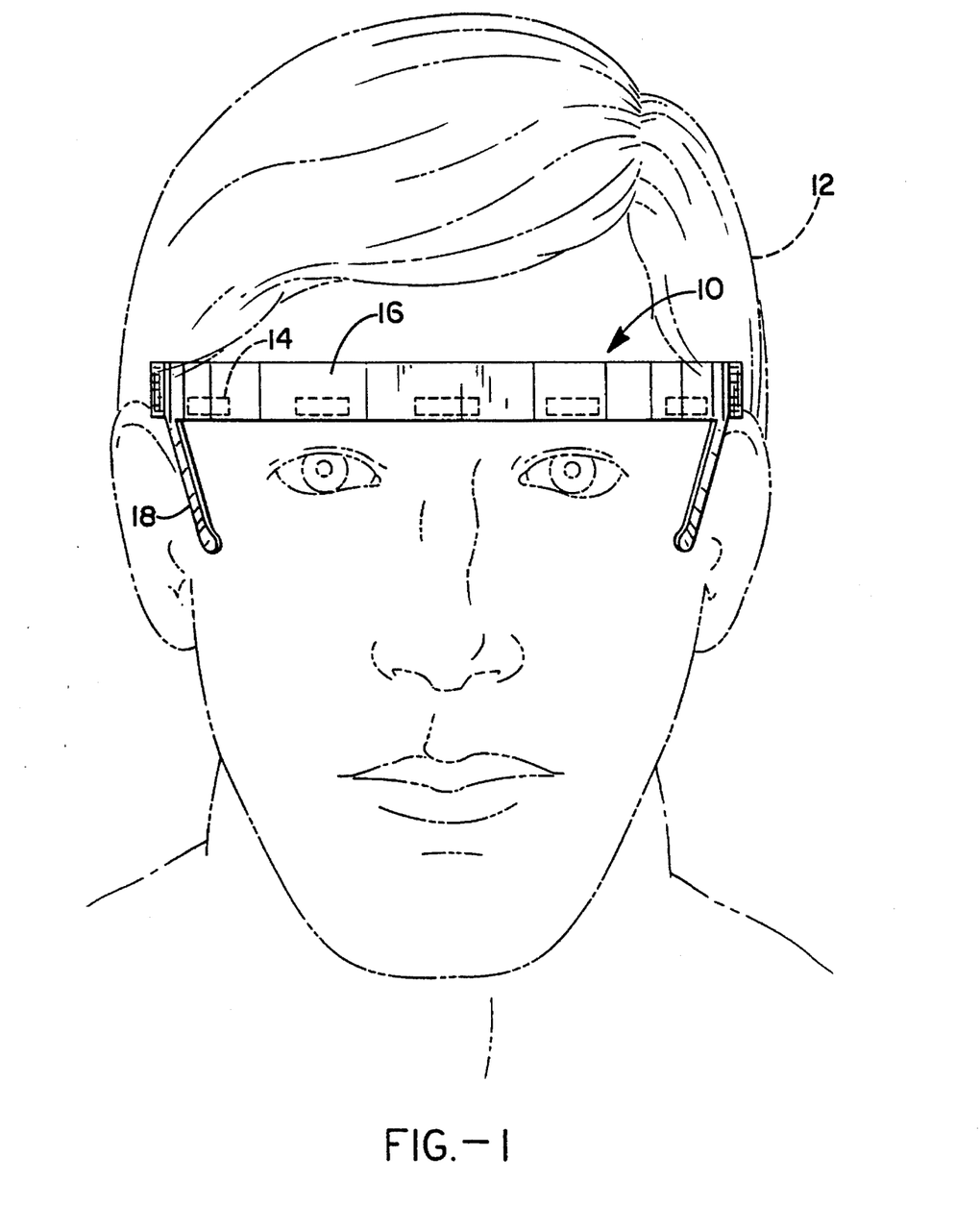
FIG. 1 is a front elevation view of the sensor headband of the present invention worn by a human operator shown in phantom.

Referring to FIG. 1, headband 10 is worn by a human operator 12. Headband 10 includes a plurality of sensors 14 which are fabricated from a flexible material such as silver-silver chloride which is suitable for conductive coupling with the skin of human operator 12. Headband 10 includes horizontal sensor support 16 and at least one vertical sensor support 18.

Referring also to FIG. 2, side straps 20a, 20b wrap around the head of human operator 12 and are supported in place by fastener 22 which is velcro or the like. Sensors 14 comprise right dual sensor 24, right vertical sensor 26, right horizontal sensor 28, left dual sensor 30, left vertical sensor 32, left horizontal sensor 34, and reference sensor 36. It should be noted that, although the positions of sensors 14 are shown in FIG. 1 and FIG. 2, these positions can be varied somewhat without adverse effect. Preferably, right horizontal sensor 28 and left horizontal sensor 34 are located at the medial position over the right and left eyes, respectively. Right dual sensor 24 and left dual sensor 20 are located at lateral or temporal positions above the right and left eye, respectively. Right vertical sensor 26 and left vertical sensor 32 are located below the eyes and generally aligned with right dual sensor 24 and left dual sensor 30. Reference sensor 36 is generally placed on the forehead in proximity to the central line of the bridge of the nose. Note also that the horizontal alignment of the sensors can be altered.

Electrically coupled to right dual sensor 24, right vertical sensor 26, right horizontal sensor 28, left dual sensor 30, left vertical sensor 32, left horizontal sensor 34, and reference sensor 36 are electrical lead 38, electrical lead 40, electrical lead 42, electrical lead 44, electrical lead 46, electrical lead 48, and electrical lead 50, respectively.

Referring now to FIG. 3A, four input channels are shown. In the embodiment wherein only eye convergence is used for three-dimensional imagery control, or where eye convergence and divergence is to be measured, two input channels are used (right horizontal and left horizontal). However, use of two input channels would limit imagery control to horizontal movement of the eyes. Therefore, it is preferred to use three input channels so that a vertical channel can be included. In this manner, vertical eye movement can move the image along the "Y" axis, horizontal eye movement can move the image along the "X" axis, and convergence can move the image along the "Z" axis (zoom in/out). In the embodiment for determining the horizontal or vertical position of each eye independently, such as in strabismus measurement, four input channels are used.

Instrumentation amplifier 52 is a single input differential amplifier and accepts positive and negative EOG signals. Right dual sensor 24 is electrically coupled to one input of instrumentation amplifier 52 through electrical lead 38 and right horizontal sensor 28 is electrically coupled to the other input through electrical lead 42. Instrumentation amplifier 52 is typically an LT1100, LT1101 or LT1102. Other devices can be used but, to achiever higher accuracy, they should exhibit four characteristics. First, the device should have a high input impedance to minimize the effects of the sensor source impedance. Second, the device should draw very little bias current from the sensors to minimize noise from the sensors as well as ionic migration of the sensors. Third, the device should have an RMS noise voltage of less than 0.35 microvolts RMS to allow for measurements of 0.5 microvolts peak input signals. Fourth, in order to remove extremely large common mode signals, the device should have a common mode rejection ratio greater than 80 decibels in the frequency of interest. Referring also to FIG. 3B, the reference input of instrumentation amplifier 52 is electrically coupled to digital to analog convertor 54 through interconnection 56. This interconnection permits an offset voltage signal to be produced for calibration of instrumentation amplifier 52.

Instrumentation amplifier 52 is electrically coupled to programmable gain amplifier 58. Programmable gain amplifier 58 typically comprises a PMI8408 quad digital to analog convertor and TL064 quad operational amplifier. This configuration is designed to have an eight bit digitally programmable gain between approximately 0.5 and 100 V/V. This permits measurement of voltage signals between 0.5 microvolts and 50 millivolts without clipping. Referring also to FIG. 3B, the gain of programmable gain amplifier is controlled by digital signal processor 60 through interconnection 62 which serves as both an address and data line. Digital signal processor 60 sends a signal to programmable gain amplifier for calibration purposes. Because the electrical value of EOG signals vary from person to person and between eyes, it is necessary to calibrate the voltage signals produced in order to achieve accurate and consistent output voltages for different eye positions. Therefore, programmable gain amplifier 58 is adjusted to produce a 5 volt output signal when the eyes are focused on calibration points. Those calibration points are typically the upper left corner and the lower right corner of a video display or sighting chart.

Programmable gain amplifier 58 is electrically coupled to low pas filter 64. Low pass filter 64 is typically a fourth order 50 Hz Butterworth filter which filters biopotential signals having frequencies above those of the desired EOG signals and only passes signals between DC and 50 Hz. The output of low pass filter 64 is electrically coupled to analog to digital convertor 66 through interconnection 68.

Each of the additional input channels utilizes the same functional components and is similarly configured as described above.

Referring now to FIG. 3B, digital to analog convertor 54 is typically a PMI8412 quad 12-bit device or equivalent. Alternatively, an AD7226 quad 8-bit device could be used. Digital to analog convertor 54 is electrically coupled to digital signal processor 60 through interconnection 82. To calibrate instrumentation amplifier 52, digital signal processor 60 sends a digital signal to digital to analog convertor 54 thereby producing an offset voltage. The offset voltage is selected such that the output of low pass filter 64 is zero volts when the eyes of human operator 12 are fixed in a straight-ahead position. This permits the DC signals from sensors 14 and the DC offsets from instrumentation amplifier 52 to be removed.

Analog to digital convertor 66 is typically an LTC1294 or equivalent and includes an 8 to 1 multiplexer, sample and hold, and successive approximation analog to digital convertor in a single package. Alternatively, a similar device having a 4 to 1 multiplexer could be used. Analog to digital convertor 66 is electrically coupled to digital signal processor 60 through interconnection 84 which is a synchronous serial interface. Analog to digital convertor 66 is clocked at 1 MHz by digital signal processor 60 through interconnection 86. This yields a 50 kHz sampling rate.

Digital signal processor 60 is typically a Texas Instrument TMS320C26 or equivalent. This device is a 10 MIPS, 16/32 bit fixed point digital signal processor capable of executing a digital filter tap in one instruction cycle. Digital signal processor 60 uses a 40 MHz clock which is divided by four to create a system clock which is available through interconnection 104. The system clock is divided by ten to create the clock signal for analog to digital convertor 66. Digital signal processor 60 includes 16K of internal memory.

Digital signal processor 60 is electrically coupled to serial interface 88 through interconnection 90. Serial interface 88 typically includes a Signetics SCC2691 UART for decoding/encoding at rates up to 38.4 kilobaud, and a MAX252 RS232 interface. Serial interface 88 permits the present invention to exchange data with and control any computer system. Digital signal processor 60 is also electrically coupled to non-volatile RAM (NVRAM) through interconnection 106 for reading and writing data as well as erasable programmable ROM (EPROM) through interconnection 108 for program storage. It should be noted that digital signal processor 60 also performs the computational functions disclosed and claimed herein. These functions include calibration of EOG output signals at reference points, conversion of EOG output signals to positional signals representing the position of the eyes, sensing EOG signals, performing numerical computations, drift compensation, and monitoring changes in polarity and amplitude of EOG output signals.

Because an input channel cannot test itself, when it is necessary to test an input channel a test signal can be produced by digital to analog convertor 54. For example, operating switch 92 will electrically couple digital to analog converter 54 to low pass filter 94 through interconnection 96. The resultant voltage signal is then attenuated by attenuator 98 and can be coupled to an input channel by interconnections 100, 102.

Referring now to FIG. 2, EOG signals representing horizontal and vertical positions of each eye are derived by measuring differential voltages between individual sensors 14 with reference to circuit ground which is electrically coupled to reference sensor 36 through interconnection 50. The following relationships determine the positions of the eye:

Right Horizontal position H1:

$H1$ equals $V_{BA}$ minus $V_{CA}$

Left Horizontal position H2:

$H2$ equals $V_{AD}$ minus $V_{AE}$

Right Vertical position V1:

$V1$ equals $V_{FA}$ minus $V_{BA}$

Left Vertical position V2:

$V2$ equals $V_{GA}$ minus $V_{EA}$ where:
H1 is the EOG voltage signal representing the horizontal position of the right eye;
H2 is the EOG voltage signal representing the horizontal position of the left eye;
V1 is the EOG voltage signal representing the vertical position of the right eye;
V2 is the EOG voltage signal representing the vertical position of the left eye;
$V_{BA}$ is the voltage differential between right dual sensor 24 and reference sensor 36;
$V_{CA}$ is the voltage differential between right horizontal sensor 28 and reference sensor 36;
$V_{AD}$ is the voltage differential between reference sensor 36 and left horizontal sensor 34;
$V_{AE}$ is the voltage differential between reference sensor 36 and left dual sensor 30;
$V_{FA}$ is the voltage differential between right vertical sensor 26 and reference sensor 36;
$V_{GA}$ is the voltage differential between left vertical sensor 32 and reference sensor 36; and
$V_{EA}$ is the voltage differential between left dual sensor 30 and reference sensor 36.

While reference sensor 36 is typically used in the determination of the vertical position of an eye, it is also possible to make such a measurement without resort to reference sensor 36 for each computation. For example, $V_{FA}$ could be determined from the voltage differential between right vertical sensor 26 and right horizontal sensor 28. $V_{BA}$, however, would still be determined from the voltage differential between right dual sensor 24 and reference sensor 36. When the eyes of human operator 12 are focused on a reference point, such as in straight ahead position, H1 minus H2 is calibrated to zero as is V1 minus V2. When the eyes of human operator 12 are converged (crossed), a change in amplitude will occur and H1 minus H2 will be greater than zero. When the eyes of human operator 12 are diverged (spread), H1 minus H2 will be less than zero. Therefore, not only can the actual position of each eye be determined relative to a fixed reference point, but it can be determined if the eyes are converged or diverged.

FIG. 4 shows the preferred process steps for using eye convergence in three-dimensional imagery applications. As discussed previously, for eye convergence measurements it is necessary to use only two input channels. However, in three-dimensional imagery it is desired to move the image along either the "X", "Y", or "Z" axis. Therefore, in preferred embodiment one input channel is used for left horizontal eye movement, one input channel is used for right horizontal eye movement, and one input channel is used for vertical eye movement (either right or left eye).

At step 120, human operator 12 focuses his or her eyes in a fixed straight-ahead position and the EOG output signals for each channel are calibrated such that H1 minus H2 equals zero. At step 122, H2 is subtracted from H1 to determine if there has been any horizontal movement of either eye in relation to the calibration position. At step 124, the numerical result from step 122 is compared with the previous value. If H1 minus H2 is greater than the previous value, then there has been movement from a converged position to a less converged position (e.g., toward alignment). In such case, at step 126 the object on a video display is moved in the third dimension along the "+Z" axis (e.g., zoom out). If H1 minus H2 is not greater than the previous value, then step 128 determines whether the value is less than the previous value. If so, then there has been movement from an less converged to a more converged position (e.g., away from alignment). In such case, at step 130 the object on a video display is moved in the third dimension along the "–Z" axis (e.g., zoom in). If H1 minus H2 is neither greater than nor less than the previous value, step 132 dictates that no movement occur. As an alternative to moving the object in the third dimension in this fashion, the convergence determination can be used to jump into hyperspace or change levels on a two-dimensional video game or simply control the operation of another device.

For strabismus measurement it is desired to determine the horizontal or vertical position of each eye independently in relation to a fixed reference point. Strabismus is typically measured using nine cardinal positions with the center cardinal position as the reference point. Deviation from alignment is measured in units of prism diopter. One degree of deviation equals 1.7 diopters and one millimeter of deviation equals 21 diopters. In order to measure the position of each eye independently, four input channels are required; right vertical, right horizontal, left vertical, and left horizontal. These positions correspond to EOG signals H1, V1, H2, and V2, respectively.

One aspect of strabismus measurement is the determination of whether the eyes of human operator 12 are converged (e.g., crossed) or diverged (e.g., spread apart) as compared to an aligned position. Referring to FIG. 5, the steps are shown for determining the degree of convergence and divergence of the eyes. At step 140, human operator 12 covers the left eye and focuses the right eye in a fixed straight-ahead position. The horizontal EOG output signal for the right eye is calibrated by setting it to zero. The same procedure is then followed for the left eye to calibrate the horizontal EOG output signal for that eye. At step 142, H2 is subtracted from H1 to determine the amount of deviation from the aligned position. At step 144, the differential voltage between right horizontal EOG signal H1 and left horizontal EOG signal H2 is measured. If the differential voltage is equal to zero, step 146 reports that the eyes are aligned. If the eyes are not aligned, at step 148 the differential voltage is tested to determine is it is greater than zero. If so, step 150 reports that the eyes are in a converged position and the degree of convergence corresponds to the absolute value of the voltage differential. If at step 148 it is determined that the voltage differential is not greater than zero (e.g., a negative differential), then step 152 reports that the eyes are in a diverged position and the degree of divergence corresponds linearly to the absolute value of the voltage differential (e.g., H2 minus H1). The same procedure is followed for calibration and measurement of vertical deviations.

In order to achieve a high degree of accuracy in the measurement of eye position using EOG signals it is necessary to compensate for drift. If, for example, the eyes of human operator 12 are maintained in a continuous fixed position, the EOG signals will drift off of the calibration level. Therefore, drift compensation is required. Referring now to FIG. 6, at step 160 the output value of any channel is initialized to a zero value. At step 162, the mathematical derivative of the output value is computed in real time. In doing so, it is critical that the time period used for computation of the derivative be short enough that the eye position is stable during the derivative window. Similarly, the time period must be long enough to avoid spurious signal changes. Such time periods are empirically determined depending on the particular use. For example, if rapid eye movement is to be measured, then a shorter derivative window is selected than for measurement of slow eye movement. At step 164, the derivative is compared with a threshold value. This threshold value is an empirically determined value based on the amount of drift from the sensors coupled to the input channel. The threshold value must be great enough to remove all drift, but small enough to permit measurement of all eye movement. If the derivative is not greater than the threshold value, step 166 causes the retention of the original output value and returns this value to step 162. If the derivative is greater than the threshold value, the original value and its derivative are numerically summed at step 168 and the summation is returned to step 162. This process is performed by digital signal processor 60.

Accordingly, it will be seen that this invention can accurately determine the horizontal and vertical position of each eye using EOG signals and use eye position to control and output device such as a video game or a computer to measure strabismus. Although the description above contains many specificities, these should not be construed as limiting the scope of the invention but as merely providing illustrations of some of the presently preferred embodiments of this invention. Thus the scope of this invention should be determined by the appended claims and their legal equivalents.

I claim:

1. A method for controlling the position of an image on a video display, comprising the steps of:

(a) sensing electro-oculogram voltage signals representing the horizontal position of a right eye in relation to a first reference point;

(b) sensing electro-oculogram voltage signals representing the horizontal position of a left eye in relation to said first reference point;

(c) determining the numerical difference between said electro-oculogram voltage signals representing the horizontal position of said right eye and said electro-oculogram signals representing the horizontal position of said left eye;

(d) successively repeating step (c);

(e) controlling the position of an image on a video display based on a change in the amplitude of the electro-oculogram signals derived in step (d).

2. The method recited in claim 1, further comprising the step of compensating for changes in amplitude of said electro-oculogram signals when said eyes are fixed in position.

3. The method recited in claim 1, further comprising the steps of:

(f) measuring the change in amplitude of each said electro-oculogram voltage signal over a fixed time interval;

(g) comparing said change in amplitude with a reference voltage signal;

(h) numerically summing said electro-oculogram voltage signal and said change in amplitude when said change in amplitude exceeds said reference voltage signal; and (i) repeating steps (f) through (h).

4. An apparatus for controlling the position of an image on a video display, comprising:

(a) right horizontal sensing means for sensing electro-oculogram voltage signals produced by horizontal movement of a right eye;

(b) left horizontal sensing means for sensing electro-oculogram voltage signals produced by horizontal movement of a left eye;

(c) means for compensating for electro-oculogram voltage signal drift when said eyes are fixed in position; and (d) processing means for processing said electro-oculogram signals to determine changes in degree of convergence between said eyes and controlling the position of an image on a video display based on said changes in degree of convergence.

5. The apparatus recited in claim 4, further comprising vertical sensing means for sensing electro-oculogram voltage signals produced by vertical movement of said eyes.

6. The apparatus recited in claim 5, wherein said processing means includes means for controlling the horizontal position of said image on said video display based on horizontal movement of said eyes and means for controlling the vertical position of said image on said video display based on vertical movement of said eyes, said degree of convergence controlling the position of said image in a third dimension.

* * * * *